US009388252B2

(12) United States Patent
Forget et al.

(10) Patent No.: US 9,388,252 B2
(45) Date of Patent: Jul. 12, 2016

(54) METHODS FOR PURIFYING POLYSACCHARIDES AND PHARMACEUTICAL COMPOSITIONS AND MEDICAL DEVICES CONTAINING THE SAME

(71) Applicants: Aurelien Forget, Mawson Lakes (AU); Venkatram Prasad Shastri, Nashville, TN (US)

(72) Inventors: Aurelien Forget, Mawson Lakes (AU); Daniel Vonwil, Freiburg (DE); Venkatram Prasad Shastri, Nashville, TN (US)

(73) Assignees: Aurelien Forget, Paris (FR); Venkatram Prasad Shastri, Nashville, TN (US)

( * ) Notice: Subject to any disclaimer, the term of this patent is extended or adjusted under 35 U.S.C. 154(b) by 0 days.

(21) Appl. No.: 14/624,294

(22) Filed: Feb. 17, 2015

(65) Prior Publication Data

US 2015/0232581 A1 Aug. 20, 2015

Related U.S. Application Data

(60) Provisional application No. 61/940,800, filed on Feb. 17, 2014.

(51) Int. Cl.

| | |
|---|---|
| ***A61K 38/18*** | (2006.01) |
| ***C08B 37/00*** | (2006.01) |
| ***A61K 31/7016*** | (2006.01) |
| ***A61K 6/097*** | (2006.01) |
| ***A61K 9/06*** | (2006.01) |
| ***C08J 3/075*** | (2006.01) |
| ***C08L 5/12*** | (2006.01) |
| ***A61K 47/36*** | (2006.01) |
| ***A61L 27/20*** | (2006.01) |
| ***A61L 27/52*** | (2006.01) |
| ***A61L 15/60*** | (2006.01) |
| ***A61K 31/729*** | (2006.01) |
| *A61K 9/00* | (2006.01) |

(52) U.S. Cl.

CPC ............. *C08B 37/0039* (2013.01); *A61K 6/097* (2013.01); *A61K 9/06* (2013.01); *A61K 31/7016* (2013.01); *A61K 31/729* (2013.01); *A61K 47/36* (2013.01); *A61L 15/60* (2013.01); *A61L 27/20* (2013.01); *A61L 27/52* (2013.01); *C08B 37/0003* (2013.01); *C08J 3/075* (2013.01); *C08L 5/12* (2013.01); *A61K 9/0019* (2013.01); *A61L 2400/04* (2013.01)

(58) Field of Classification Search

CPC . A61K 31/729; A61K 31/7016; A61K 6/097; A61K 9/06; A61K 47/36; A61K 9/0019; A61L 27/20; A61L 15/60; A61L 2400/14; A61L 27/52; C08B 37/003; C08B 37/0039; C08L 5/12; C08L 1/00; C08J 3/075

See application file for complete search history.

(56) References Cited

U.S. PATENT DOCUMENTS 4,290,911 A * 9/1981 Cook et al. .................... 204/456
6,287,765 B1 * 9/2001 Cubicciotti ............ C07H 21/00 435/6.1

OTHER PUBLICATIONS

Fernandez-Cossio et al ("Biocompatibility of Agarose Gel as a Dermal Filler: Histologic Evaluation of Subcutaneous Implants", Plast. Reconst, Surg. 120: 1161, 2007).*

Bazaka, et al., "Bacterial Extracellular Polysaccharides" , Bacterial Adhesion, Advances in Experimental Medicine and Biology, 715, D. Linke, A. Goldman (eds.),pp. 213-26 (2011).

Beenken-Rothkopf,et al. (2012) "Protein polymer hydrogels" : Effects of endotoxin on biocompatibility, J Biomaterials Applications,0(0) 1-12 (2012).

European Medicines Agency, "ICH Topic Q3C ( R4) Impurities" : Guideline for Residual Solvents, pp. 1-22 (2010).

FDA, "Bacterial/endotoxins programs" , available at : http://www.fda.gov/ICECl/InspectionGuides/InspectionTechnicalGuides/ucm072918., available Jan. 12, 1979, accessed May 20, 2015.

Fernandez-Cossio, et al., "Biocompatibility of agarose gel as a dermal filler: hisrologic evaluation of subcutaneous implants" , Plastic and Reconstructive Surgery, 120:1161-9 (2007).(Abstract Only).

Forget, et al., "Polysaccharide hydrogels with tunable stiffness and provasculogenic properties via a-helix to $^2$-sheet switch in secondary structure" , PNAS, 110(32)1 2877-92 (2013).

Goldman, et al., "The effects of gamma radiation sterilization and ageing on the structure and morphology of medical grade ultra high molecular weight polyethylene" , Polymer, 37:2909-13 (1996).

Gulrez, et al., "Hydrogels" : Methods of Preparation , Characterisation and Application http://www.intechopen.com, pp. 1-35, (2003).

Hirayama and Sakata, "Chromatographic removal of endotoxin from protein solutions by polymer particles" , J Chromatography B, 781:419-32 (2002).

Huebsch, et al., "Analysis of Sterilization Protocols for Peptide-Modified Hydrogels" , Materials Sci.,781:440-7 (2005).

Lambert, et al., "Radiation and ethylene oxide terminal sterilization experiences with drug eluting stent products" , AAPS PharmSciTech., 12:1116-26 (2011).

Mendes, et al., Ethylene oxide sterilization of medical devices: a review. Am J Infect Control, 35:574-81 (2007).

Munarin, et al., "Sterilization treatments on polysaccharides: Effects and side effects on pectin" , Food Hydrocolloids, 31:74-84 (2013).

(Continued)

*Primary Examiner* — Suzanne Ziska

(74) *Attorney, Agent, or Firm* — Pabst Patent Group LLP

(57) ABSTRACT

Methods for removing endotoxin from naturally occurring materials, such as polysaccharides (e.g., agarose and/or carrageenan) are described herein. Polysaccharides that are substantially free of endotoxins and uses thereof are also described. The polysaccharide materials can be isolated from microorganisms, multicellular organisms, such as, algae, plants, seaweed, etc. The method involves the use of acidic and basic solutions to hydrolyze the lipid-polysaccharide bond in endotoxins. Cleaving the fatty acid from the polysaccharide reduces the water-solubility of the fatty acid and enables its removal with an organic solvent such as ethanol. The polysaccharide component can also undergo acidic or basic hydrolysis due to the weak glycosidic bond between the sugar rings.

6 Claims, 4 Drawing Sheets

(56) References Cited

OTHER PUBLICATIONS

Rederstorff, et al., "Sterilization of exopolysaccharides produced by deep-sea bacteria: impact on their stability and degradation", Marine Drugs, 9:224-41 (2011).

Serdons, et al., "The presence of ethanol in radiopharmaceutical injections" , J Nuclear Med., 49:2071 (2008).

Sintzel, et al., "Influence of Irradiation Sterilization on Polymers Used as Drug Carriers" A Review, Drug Dev Indust Pharm., 23:857-878 (1998).

Suzawa, et al., "Regenerative behavior of biomineral/agarose composite gels as bone grafting materials in rat cranial defects" , J Biomed Mat Res. Part A, 93:965-75 (2010).

Tyan, et al., "The study of the sterilization effect of gamma ray irradiation of immobilized collagen polypropylene nonwoven fabric surfaces" , J Biomed Mat Res Part A, 67:1033-43 (2003).

Van Doornmalen and Kopinga, "Review of surface steam sterilization for validation purposes" , Am J Infect Control., 36:86-92 (2008).

* cited by examiner

| | Mean | STDV |
|---|---|---|
| Silicone | 9,50% | 0,38% |
| Medical steel | 19,50% | 1,17% |
| Agarose sterile | 3,90% | 0,04% |

METHODS FOR PURIFYING POLYSACCHARIDES AND PHARMACEUTICAL COMPOSITIONS AND MEDICAL DEVICES CONTAINING THE SAME

CROSS-REFERENCE TO RELATED APPLICATION

This application claims priority to U.S. Provisional Application No. 61/940,800, filed Feb. 17, 2014, the disclosure of which is incorporated herein in its entirety.

FIELD OF THE INVENTION

This invention is in the field of methods for the purification of naturally occurring materials having clinical importance, particularly the removal of endoxtoxins.

BACKGROUND OF THE INVENTION

Medical devices, such as dermal fillers or implants made from naturally occurring materials including polysaccharides, are in direct contact with organ tissue and therefore must be made from biocompatible materials. Such materials have to (1) be inert, (2) induce little or no immune response, and (3) in some cases be degradable by the organism. Unfortunately, medical devices can be contaminated during their manufacturing, transportation and/or storage. Contamination such as by microorganisms (e.g., bacteria, virus or spores) or chemicals can induce inflammatory responses, which can lead to fever, hypotension, systemic shock and even death. Moreover, many of these materials are isolated from naturally occurring sources, such as microorganisms, and typically contain unacceptable levels of endotoxins. Therefore, the successful translation of medical devices to the clinic requires ensuring their safety until implantation.

One of the most serious contaminations that can occur in medical devices prepared from naturally occurring materials, such as polysaccharides, is endotoxins. Endotoxins are integral components of Gram-negative bacterial cell walls. Endotoxins are exogenous pyrogenic substances, i.e. they can induce fever. Endotoxins typically contain a polysaccharide chain, which is water soluble, bound to a hydrophobic or water-insoluble lipid strand. A representative structure for an endotoxin is shown in FIG. 6:

Due to their amphiphilicity, endotoxins are difficult to remove from commercially useful materials.

Several sterilization processes are commonly used to prevent contamination including filtration, gamma irradiation, ethylene oxide, steam, and chemical sterilization. These procedures are able, to varying degrees, to kill microorganisms (bacteria and mammalian cells), destroy viruses (protein carriers of genetic information such as DNA or RNA), or degrade endotoxins (lipopolysaccharides originating from bacteria wall). Autoclaving, which is a common technique used for sterilization, cannot remove endotoxins. Moreover, the removal of endotoxins from commercially useful materials, such as agarose or carrageenan, is challenging since these materials themselves are polysaccharides. Moreover, these techniques can also generate degradation products of the material, which can be toxic, or causes changes to its mechanical properties, affecting the proper operation of the device. A summary of the drawbacks of various sterilization techniques is shown in Table 1.

TABLE 1

Advantages and drawbacks of the different sterilization methods

| Technique | Sterility* | Endotoxin | Material mechanical properties preservation | Cost |
|---|---|---|---|---|
| Filtration | +/+/− | − | + | $ |
| Irradiation | +/+/+ | − | − | $$$ |
| Ethylene Oxide | +/+/+ | − | − | $$$ |
| Steam | +/+/− | −− | ++ | $$ |
| Ethanol | +/−/− | + | +++ | $ |

*Bacteria/Virus/Spores

Irradiation and EO are two techniques that are fast and quite efficient for removal of viruses and endotoxins. Unfortunately they cannot be used for the sterilization of polysaccharide, such as agarose, as they modify the polysaccharide backbone. Therefore specific considerations of the sterilization method have to be taken into account for obtaining a material that meets the requirements of regulatory agencies. Table 2 shows some of the requirements of the Food and Drug Administration (FDA) in the United States for clinical grade materials.

TABLE 2

Some of the requirement for clinical grade materials

| | Level Regulation | Source | Ref. |
|---|---|---|---|
| Ethanol Content | <0.5% v/v | FDA | (1) |
| Microbiology | N.D. | FDA | |
| Endotoxins | <0.05 EU/ml | FDA | (2) |

(1) Serdons, et al. *Journal of Nuclear Medicine: Official Publication, Society of Nuclear Medicine* 2008; 49: 2071
(2) FDA Bacterial/Endotoxins Pyrogens. Available at http://www.fda.gov/ICECI/InspectionGuides/InspectionTechnicalGuides/ucm072918.htm#.Ug0qTDAoFos.email Dialysis of naturally occurring materials material against pyrogen free water has been explored to overcome the limitations of the techniques discussed above. Dialysis, however, is an expensive and time consuming process.

There exists a need for improved methods for removing endotoxin from naturally occurring materials, such as polysaccharides.

Therefore, it is an object of the invention to provide for improved methods for removing endotoxin from naturally occurring materials, such as polysaccharides.

It is also an object of the invention to provide for improved methods for removing endotoxin from naturally occurring materials, such as polysaccharides, which are cost effective and can be performed over a relatively short period of time.

It is also an object of the invention to provide for improved methods for removing endotoxin from naturally occurring materials, such as polysaccharides, which are cost effective and can be performed over a relatively short period of time, and which do not significantly alter the chemical, physical, and/or mechanical properties of the material.

SUMMARY OF THE INVENTION

Methods for removing endotoxin from naturally occurring materials, such as polysaccharides (e.g., agarose and/or carrageenan) are described herein. The materials can be isolated from microorganisms, multicellular organisms, such as, algae, plants, seaweed, etc. The method involves the use of acidic and basic solutions to hydrolyze the lipid-polysaccharide bond in endotoxins. Cleaving the fatty acid from the polysaccharide reduces the water-solubility of the fatty acid and enables its removal with an organic solvent such as ethanol. The polysaccharide component can also undergo acidic or basic hydrolysis due to the weak glycosidic bond between the sugar rings.

The acceptable endotoxin level unit concentration (EU/ml) established by the Food and Drug Administration (FDA) in the United States for medical devices is 0.05 EU/ml or 20 EU/device. The endotoxin level of commercially available agarose after steam sterilization has an EU level above FDA standards. However, after the endotoxin removal procedure described herein and autoclaving, the endotoxins level was about 0.02 EU/ml.

The mechanical properties of the hydrogel after the procedure described herein were assessed. The entire process, purification and packaging, was performed manually, and therefore this assessment also took into account the operator error leading to variations in syringe loading. The mechanical testing reveals that there were no significant changes in the hydrogel properties between the untreated and the purified product. This suggests that the use of acidic and basic solutions and steam sterilization does not alter the agarose backbone.

The hemolytic properties of the agarose was compared to silicone and medical (surgical steel) using the 24 h lysis test available from HaemoScan. The amount of lysis induced by agarose was 3.9%/$cm^2$, which is considered acceptable according to ISO 10993-4 (<5%).

DETAILED DESCRIPTION OF THE INVENTION

I. Definitions

Figure 1:
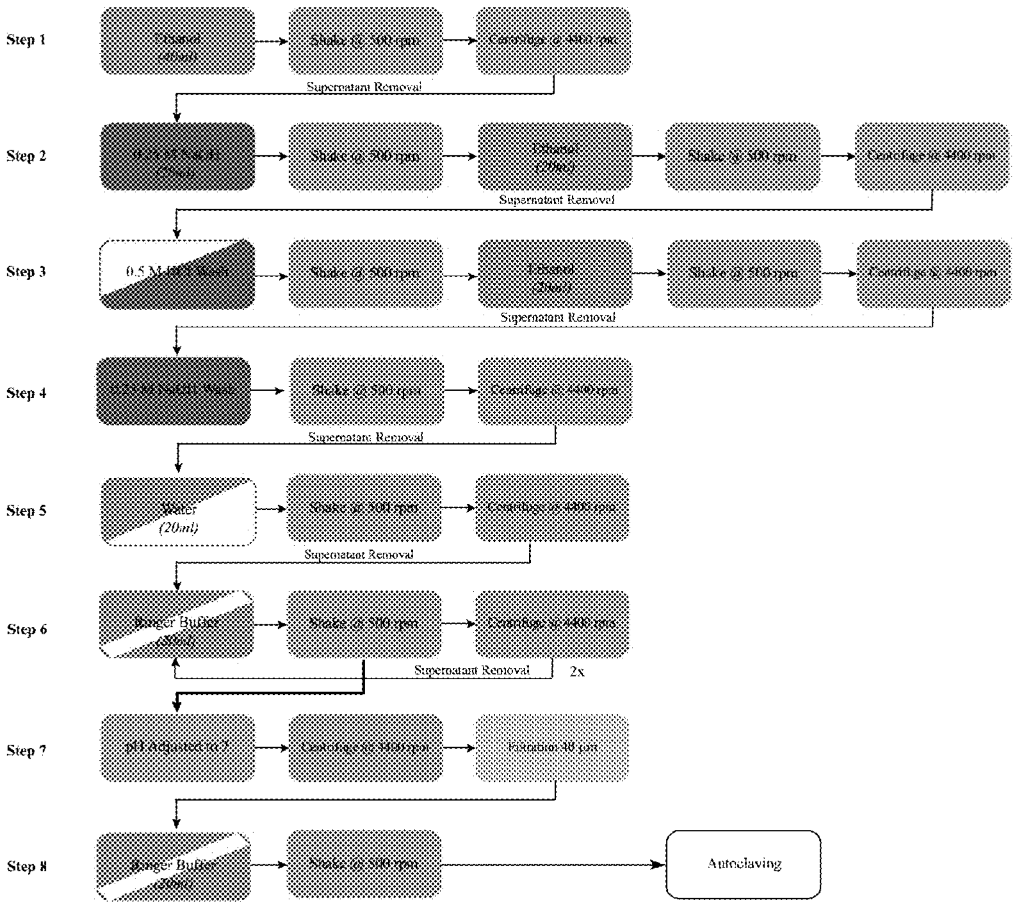
FIG. 1 is a flow chart describing one embodiment of the isolation and purification procedure described herein.

"Polysaccharide derivative" as used herein refers to a polysaccharide that possesses the same core as the parent compound, but differs from the parent compound, with one or more substituents attached to the core, which may include one or more atoms, functional groups, or substructures. In general, a derivative can be imagined to be formed, at least theoretically, from the parent compound via chemical and/or physical processes. Typically in a polysaccharide derivative the constituent saccharide moieties are substituted by one or more substituents that differ from those of the parent polysaccharide. Exemplary substituents include but are not limited to carboxylate, phosphate, sulfate, and sulfonate groups, and combinations of such groups.

"Agarose derivative," as used herein refers to a molecule that has substantially the same basic structure as agarose (i.e., alternating D-galactose and 3,6-anhydro-L-galactopyranose linked by α-(1→3) and β-(1→4) glycosidic bonds) wherein the constituent saccharide moieties are substituted by one or more substituents that differ from those of agarose. Exemplary substituents include but are not limited to carboxylate, phosphate, sulfate, and sulfonate groups, and combinations of such groups.

"Substantially free of endotoxin", as described herein, means that in endotoxin free water placed on top of an equivalent volume of a 2% polysaccharide sample (2 day exposure) less than 0.05 Endotoxin Units can be found per milliliter.

The term "targeting moiety" as used herein refers to a moiety that localizes to or away from a specific locale. The moiety may be, for example, a protein, nucleic acid, nucleic acid analog, carbohydrate, or small molecule. The entity may be, for example, a therapeutic compound such as a small molecule, or a diagnostic entity such as a detectable label. The locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

"Adhesion site", as used herein, refers to a peptide sequence to which a molecule, for example, an adhesion-promoting receptor on the surface of a cell, binds. Examples of adhesions sites include, but are not limited to, the RGD sequence from fibronectin, and the YIGSR sequence from laminin. Preferably adhesion sites are incorporated into the biomaterial of the present invention "Growth factor", as used herein refers to endogenous or synthetic peptides or proteins that impact status of mammalian cells, such as cell cycle, proliferation, differentiation, and/or cell death. Exemplary growth factors include but are not limited to heparin-binding growth factors (HBGFs). HBGFs are a large class of growth factors that include the 23 fibroblast growth factors identified to date (FGFs 1-23), HBBM (heparin-binding brain mitogen), HB-GAF (heparin-binding growth associated factor), HB-EGF (heparin-binding EGF-like factor) HB-GAM (heparin-binding growth associated molecule), TGF-α (transforming growth factor-α), TGF-βs (transforming growth factor-βs), PDGF (platelet-derived growth factor), EGF (epidermal growth factor), VEGF (vascular endothelial growth factor), IGF-1 (insulin-like growth factor-1), IGF-2 (insulin-like growth factor-2), HGF (hepatocyte growth factor), IL-1 (interleukin-1), IL-2 (interleukin-2), IFN-α (interferon-α), IFN-γ (interferon-γ), TNF-α (tumor necrosis factor-α), SDGF (Schwannoma-derived growth factor) and many other growth factors such as, cytokines, lymphokines and chemokines that have an affinity for heparin.

"Growth factor binding site", as used herein, refers to a peptide sequence to which a growth factor, or a molecule(s) which binds a growth factor binds. For example, the growth factor binding site may include a heparin binding site. This site will bind heparin, which will in turn, bind heparin-binding growth factors, for example, bFGF, VEGF, BMP, or TGFβ.

"Protease binding site", as used herein, refers to a peptide sequence which is a substrate for an enzyme.

II. Methods for Removal of Endotoxin

Methods for removing endotoxin from naturally occurring materials, such as polysaccharides (e.g., agarose and/or carrageenan) are described herein. The materials can be isolated from microorganisms, multicellular organisms, such as, algae, plants, seaweed, etc. The method involves the use of acidic and basic solutions to hydrolyze the lipid-polysaccharide bond in endotoxins. Cleaving the fatty acid from the polysaccharide reduces the water-solubility of the fatty acid and enables its removal with an organic solvent such as ethanol. The polysaccharide component of the endotoxin can also undergo acidic or basic hydrolysis due to the weak glycosidic bond between the sugar rings.

Figure 6:
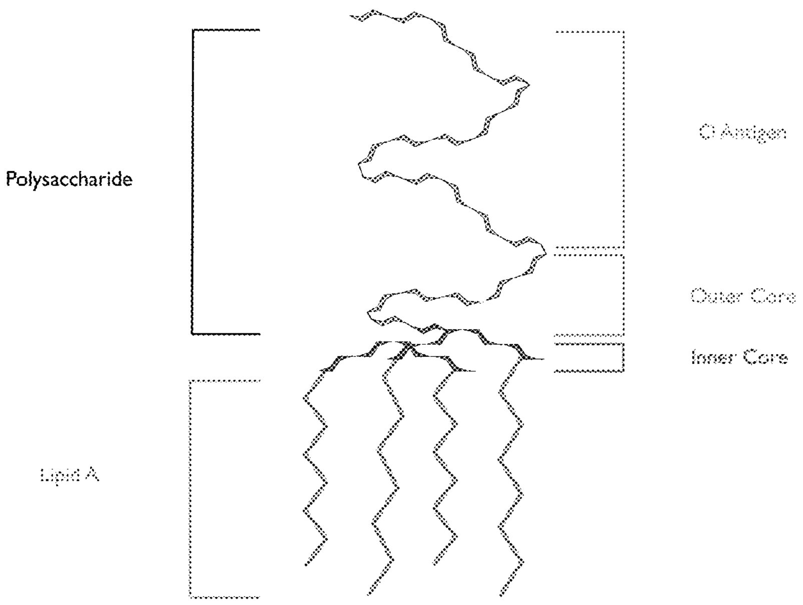
FIG. 6 is a representative structure of an endotoxin, having a water soluble polysaccharide chain bound to a hydrophobic lipid strand.

In some embodiments, the method is as follows. Step 1 involves disruption of the bacteria to free the endotoxin and solubilize the lipid portion of the endotoxin (i.e. Lipid A in FIG. 6). In some embodiments, the material to be purified, such as a naturally occurring polysaccharide, is dissolved in an organic solvent. The solvent should be biocompatible and volatile so that it is easily removed. In some embodiments, the organic solvent is an aliphatic alcohol, such as ethanol, n-propanol, isopropanol, or glycerol. Non-alcoholic solvents, such as acetone, may also be used. In some embodiments, the aliphatic alcohol is ethanol. The solution of the material to be purified can be agitated, such as by stirring, shaker tray, or sonication. Once this step is complete, the material is isolated, typically as a solid, using techniques known in the art, such as centrifugation and removal of the supernatant.

Once the lipid portion of the endotoxin has been removed, the lipid inner core bond must be hydrolyzed to release and solubilize the polysaccharide component of the endotoxin. This hydrolysis can be achieved by a series of base- and acid-catalyzed hydrolyses. In one embodiment, the solid from step 1 is dispersed or suspended in a basic solution. Any base can be used. In some embodiments, the base is an inorganic base, such as sodium hydroxide, potassium hydroxide, or calcium hydroxide. In some embodiments, the base is sodium hydroxide.

The strength of the base solution can vary. However, it is preferable that the strength is sufficiently low that it does not degrade the material to be purified, e.g., the polysaccharide backbone (such as, for example, the agarose backbone). In some embodiments, the strength of the basic solution is from about 0.01 to about 2M, preferably from about 0.1M to about 0.5M. In some embodiments, the strength is 0.25M. The free lipids are removed by washing with an organic solvent, such as an aliphatic alcohol (e.g., ethanol). Once this step is complete, the material is isolated, typically as a solid, using techniques known in the art, such as centrifugation and removal of the supernatant.

Once the first base hydrolysis step is complete, acid-hydrolysis is performed to cleave the lipid/inner core bond that was not cleaved under basic conditions. Any acid can be used. In some embodiments, the acid is a mineral acid, such as hydrochloric acid, sulfuric acid, citric acid, acetic acid, or formic acid. In some embodiments, the acid is hydrochloric acid.

The strength of the acid solution can vary. However, it is preferable that the strength is sufficiently low that it does not degrade the material to be purified, e.g., the polysaccharide backbone. In some embodiment, the strength of the acid solution is from about 0.01 to about 2M, preferably from about 0.1M to about 1M. In some embodiments, the strength is 0.5M. Optionally, free lipids may be removed by washing with an organic solvent, such as an aliphatic alcohol (e.g., ethanol). Once this step is complete, the material is isolated, typically as a solid, using techniques known in the art, such as centrifugation and removal of the supernatant.

One the acid hydrolysis step is completed, a second base hydrolysis step is performed. The second base hydrolysis step is performed as described above to complete the hydrolysis of the lipid/inner core bond and to neutralize any residual acid from the previous step. The base can be the same base as above or a different base and the strength can be the same or different. Once this step is complete, the material is isolated, typically as a solid, using techniques known in the art, such as centrifugation and removal of the supernatant.

Once the acid/base hydrolysis steps are complete, the solid material to be purified is dispersed or suspended in sterile water to remove polysaccharide component of the endotoxin and neutralize residual acid and/or base. Once this step is complete, the material is isolated, typically as a solid, using techniques known in the art, such as centrifugation and removal of the supernatant. The material to be purified can be dissolved in an autoclavable physiological buffer, such as Ringer Buffer) for additional neutralization of residual acid and/or base. Once this step is complete, the material is isolated, typically as a solid, using techniques known in the art, such as centrifugation and removal of the supernatant.

The purified material can be assayed for endotoxin levels, residual solvent levels, presence of microbiological organisms, and the mechanical properties of the material (e.g., hydrogel-forming materials).

The endotoxin level unit concentration (EU/ml) established by the Federal Drug Agency (FDA) is 0.05 EU/ml. The endotoxin level of commercially available agarose after steam sterilization (but not purified as described herein) exhibited an EU level above FDA standards. However, after endotoxin removal using the procedure described herein and autoclaving, the endotoxins level was about 0.02 EU/ml. The assay for residual solvent showed levels less than 0.2% v/v, which is less than the 0.5% v/v established by the FDA. Agarose that was purified as described herein and autoclaved showed no growth of bacterial colonies after incubation for up to one week in Luria Broth (LB).

When the purified material is to be used for structural applications, such as artificial tissue, to mimic extracellular matrices, etc., the mechanical properties of the material are critical. Mechanical testing revealed that there were no significant changes in the hydrogel properties between the commercial untreated agarose and the agarose purified as described herein. This suggests that procedure described herein did not alter the agarose backbone.

After the purification described above, the material can be stored until needed. However, if the material is to be used immediately, the material can be dissolved in a suitable solvent, such as sterilized water, the pH adjusted if necessary to 7, and the solution filtered through a filter (e.g., 40 micron pore size) to remove any insoluble submicron impurities. The volume of the solution can be adjusted to obtain the desired concentration of material, e.g., 2% w/v, and loaded in autoclavable devices, such as syringes. The syringes are autoclaved to sterilize the syringe and solubilize the material. Upon cooling, the material, if it is hydrogel-forming, will gel which is a convenient phase for storage.

The procedure described above can be used to remove endotoxin for a variety of naturally occurring materials. In some embodiments, the material is a hydrogel-forming material. In some embodiments, the naturally occurring material is a polysaccharide, such as hydrogel-forming polysaccharides. In some embodiments, the polysaccharide is agarose or carrageenan. The structures of agarose and carrageenan are shown below:

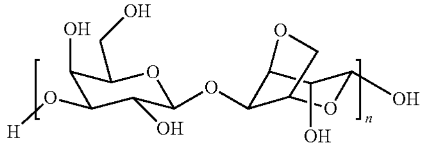

Agarose

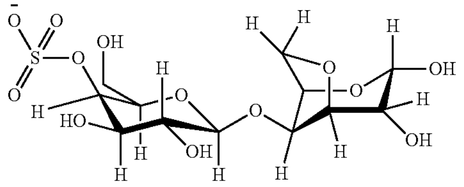

k-carrageenan structure

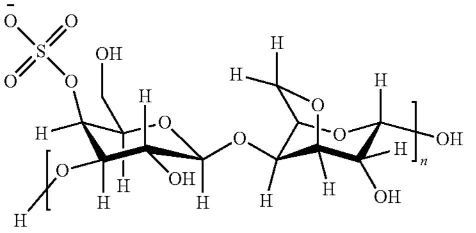

An agarose is a polysaccharide polymer material, generally extracted from seaweed. Agarose is a linear polymer made up of the repeating unit of agarobiose, which is a disaccharide made up of D-galactose and 3,6-anhydro-L-galactopyranose. Agarose is one of the two principal components of agar, and is purified from agar by removing agar's other component, agaropectin.

Agarose is a linear polymer with a molecular weight of about 120,000, consisting of alternating D-galactose and 3,6-anhydro-L-galactopyranose linked by α-(1→3) and β-(1→4) glycosidic bonds. The 3,6-anhydro-L-galactopyranose is an L-galactose with an anhydro bridge between the 3 and 6 positions, although some L-galactose units in the polymer may not contain the bridge. Some D-galactose and L-galactose units can be methylated, and pyruvate and sulfate are also found in small quantities.

Each agarose chain contains ~800 molecules of galactose, and the agarose polymer chains form helical fibers that aggregate into supercoiled structure with a radius of 20-30 nm. The fibers are quasi-rigid, and have a wide range of length depending on the agarose concentration. When solidified, the fibers form a three-dimensional mesh of channels of diameter ranging from 50 nm to >200 nm depending on the concentration of agarose used. The 3-D structure is held together with hydrogen bonds and can therefore be disrupted by heating back to a liquid state.

Agarose is available as a white powder which dissolves in near-boiling water, and forms a gel when it cools. Agarose gels and melts at different temperatures, and the gelling and melting temperature vary depending on the type of agarose. Standard agaroses derived from *Gelidium* have a gelling temperature of 35-38° C. and a melting temperature of 90-95° C., while those derived from *Gracilaria* have a gelling temperature of 40-42° C. and a melting temperature of 85-90° C. The melting and gelling temperature may be dependent on the concentration of the gel, particularly at low gel concentration of less than 1%. The gelling and melting temperature is therefore given at a specified concentration.

In some embodiments, the constituent saccharide moieties of agarose may be substituted by one or more substituents that differ from those of naturally occurring agarose to form a chemically modified agarose derivative. Exemplary substituents include but are not limited to carboxylate, phosphate, sulfate, or sulfonate groups, or combinations such groups.

Natural agarose contains uncharged methyl groups. The extent of methylation is directly proportional to the gelling temperature. Synthetic methylation, however, has the reverse effect, whereby increased methylation lowers the gelling temperature. A variety of chemically modified agarose derivatives with different melting and gelling temperatures are available; these are often made by hydroxyethylation of agarose. In certain embodiments, a carboxylated agarose derivative, depending on the degree of carboxylation, may have a variable gelation temperature as low as 10° C. (see Forget, et al. Proceedings of the National Academy of Sciences, 2013; 110(32):12877-12892). An agarose gel or chemically modified agarose derivative gel can also have high gel strength at a low concentration, such as in the range of 0.5-2.0%. Gel strength, refers to the force (Pascals) that must be applied to fracture a gel, such as an agarose gel, of a standard concentration.

Agarose can be used for medical applications in different forms, including an injectable viscous suspension for dermal filling or as a hydrogel patch for a variety of applications, such as cartilage repair. Agarose can also be used to mimic extracellular matrices. Agarose, due to its insolubility in water at room temperature, undergoes hydrolysis only at high temperature. Therefore use of low concentrated basic or acidic solution at room temperature or lower as described above should not degrade agarose. Moreover, endotoxins are of low molecular weight (e.g., 1-10 kDa), are partially soluble in water, and can be efficiently separated from the higher molecular weight, immiscible in cold water, agarose (e.g., 120 kDa) by filtration.

Carrageenans are a family of linear sulfated polysaccharides that are extracted from red edible seaweeds. They are widely used in the food industry, for their gelling, thickening, and stabilizing properties. All carrageenans are high-molecular-weight polysaccharides made up of repeating galactose units and 3,6-anhydrogalactose (3,6-AG), both sulfated and nonsulfated. The units are joined by alternating alpha 1-3 and beta 1-4 glycosidic linkages. Carrageenans are large, highly flexible molecules that curl forming helical structures. This gives them the ability to form a variety of different gels at room temperature.

There are three main varieties of carrageenan, which differ in their degree of sulfation. The primary differences that influence the properties of kappa, iota, and lambda carrageenan are the number and position of the ester sulfate groups on the repeating galactose units. Kappa-carrageenan has one sulfate per disaccharide. Iota-carrageenan has two sulfates per disaccharide. Lambda carrageenan has three sulfates per disaccharide. Higher levels of ester sulfate lower the solubility temperature of the carrageenan and produce lower strength gels, or contribute to gel inhibition (lambda carrageenan). All are soluble in hot water, but in cold water, only the lambda form (and the sodium salts of the other two) are soluble. Kappa forms strong, rigid gels in the presence of potassium ions. Iota forms soft gels in the presence of calcium ions. Lambda does not gel, and is used as a thickening agent.

III. Applications

The purified polysaccharides described herein can be used for a variety of applications, particularly applications where endotoxin levels must be below regulatory standards, such as consumable products (e.g., foods, beverages, etc.), pharmaceutical compositions for drug delivery. In certain embodiments, the purified polysaccharides and one or more pharmaceutically acceptable carriers form a drug carrier to deliver therapeutic and/or prophylactic agents. In other embodiments, the purified polysaccharides are used in a variety of medical devices, such as but not limited to wound dressings, hemostatic materials, dermal, bone, or teeth fillers, implantable gels, devices for cell delivery, and other implantable devices.

In some embodiments, the purified polysaccharide or derivative forms a hydrogel in vivo, such as when the hydrogel is administered to a patient, such as when it is placed subdermally (below the skin), adjacent to bone, adjacent to cartilage, or placed intramuscularly (within muscle). In other embodiments, the purified polysaccharide or derivative forms a hydrogel prior to administration to a patient. For example, the polysaccharide hydrogel may be loaded with one or more cells or therapeutic or prophylactic agents to form an implantable drug delivery device and implanted in a patient. Optionally, the hydrogel may be implanted in a patient subdermally (below the skin), adjacent to bone, adjacent to cartilage, or placed intramuscularly (within muscle). In some embodiments, the hydrogel implanted in the patient can be used to induce angiogenesis and/or vascular formation.

A. Pharmaceutical Compositions

In some embodiments, the polysaccharides are used as controlled release materials to provide sustained and/or delayed release of one or more therapeutic, prophylactic, and/or diagnostic agents. The agents can be encapsulated in or dispersed with the polysaccharide, particular hydrogel forming polysaccharides, and/or the agent can be covalently or non-covalently bound or associated with the polysaccharide. For example, the polysaccharide can be chemically modified to introduce one or more reactive functional groups to which can be bound or associate one or more active agents, targeting moieties, and/or other groups.

The compositions can be formulated as microparticles or nanoparticles which form a hydrogel upon contact with biological fluids. The particles can be administered by any route of administration, such as enteral (e.g., oral) or parenteral.

Exemplary classes of agents include, but are not limited to, anti-analgesics, anti-inflammatory drugs, antipyretics, antidepressants, antiepileptics, antiopsychotic agents, neuroprotective agents, anti-proliferatives, such as anti-cancer agents (e.g., taxanes, such as paclitaxel and docetaxel; cisplatin, doxorubicin, methotrexate, etc.), growth factors, anti-infectious agents, such as antibacterial agents and antifungal agents, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated. These may be vitamins, supplements such as calcium or biotin, or natural ingredients such as plant extracts or phytohormones.

The agents can be small molecules, i.e., organic, inorganic, or organometallic agents having a molecule weight less than 2000, 1500, 1200, 1000, 750, or 500 amu, biomolecules or macromolecules (e.g., having MW greater than 2000), or combinations thereof.

Examples of small molecule therapeutic agents include, but are not limited to, acyclovir, amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluorometholone, rimexolone, anecortave, cyclosporine, methotrexate, tacrolimus and combinations thereof.

In one embodiment, the particles/liposomes contain an anti-tumor agent. Classes of antitumor agents include, but are not limited to, angiogenesis inhibitors, DNA intercalators/crosslinkers, DNA synthesis inhibitors, DNA-RNA transcription regulators, enzyme inhibitors, gene regulators, microtubule inhibitors, and other antitumor agents.

Examples of angiogenesis inhibitors include, but are not limited to, Angiostatin K1-3, DL-α-Difluoromethyl-ornithine, Endostatin, Fumagillin, Genistein, Minocycline, Staurosporine, (±)-Thalidomide, revlimid, and analogs and derivatives thereof.

Examples of DNA intercalators/cross-linkers include, but are not limited to, Bleomycin, Carboplatin, Carmustine, Chlorambucil, Cyclophosphamide, cis-Diammineplatinum (II) dichloride (Cisplatin), Melphalan, Mitoxantrone, Oxaliplatin, analogs and derivatives thereof.

Examples of DNA-RNA transcription regulators include, but are not limited to, Actinomycin D, Daunorubicin, Doxorubicin, Homoharringtonine, Idarubicin, and analogs and derivatives thereof.

Examples of enzyme inhibitors include, but are not limited to, S(+)-Camptothecin, Curcumin, (−)-Deguelin, 5,6-Dichlorobenz-imidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, Tyrphostin AG 879, and analogs and derivatives thereof.

Examples of gene regulators include, but are not limited to, 5-Aza-2'-deoxycytidine, 5-Azacytidine, Cholecalciferol (Vitamin D3), Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, Troglitazone, and analogs and derivative thereof.

Examples of microtubule inhibitors include, but are not limited to, Colchicine, Dolastatin 15, Nocodazole, Paclitaxel, docetaxel, Podophyllotoxin, Rhizoxin, Vinblastine, Vincristine, Vinorelbine (Navelbine), and analogs and derivatives thereof.

Examples of other antitumor agents include, but are not limited to, 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, Urinary trypsin inhibitor fragment (Bikunin), and analogs and derivatives thereof.

In other embodiments, the agent is a biomolecule, such as a nucleic acid, protein, peptide, growth factor, etc.

Examples of classes of growth factors and growth-factor like peptides include, but are not limited to, FGF, TGF β, BMPs, IGFs, VEGFs, NGF, BDNF, HGH and PDGFs. Examples of specific growth factors or growth factor-like peptides include, but are not limited to, BMP 2, BMP 7, TGF β1, TGF β3, FGF-2, NGF, IGF 1, IGF 2 PDGF AB, human growth releasing factor, PTH 1-84, PTH 1-34 and PTH 1-25.

The nucleic acid can alter, correct, or replace an endogenous nucleic acid sequence. The nucleic acid is used to treat cancers, correct defects in genes in other pulmonary diseases and metabolic diseases affecting lung function, genes such as those for the treatment of Parkinson's and ALS where the genes reach the brain through nasal delivery.

Gene therapy is a technique for correcting defective genes responsible for disease development. Researchers may use one of several approaches for correcting faulty genes: A normal gene may be inserted into a nonspecific location within the genome to replace a nonfunctional gene. An abnormal gene can be swapped for a normal gene through homologous recombination. The abnormal gene can be repaired through selective reverse mutation, which returns the gene to its normal function. The regulation (the degree to which a gene is turned on or off) of a particular gene can be altered.

The nucleic acid can be a DNA, RNA, a chemically modified nucleic acid, or combinations thereof. For example, methods for increasing stability of nucleic acid half-life and resistance to enzymatic cleavage are known in the art, and can include one or more modifications or substitutions to the nucleobases, sugars, or linkages of the polynucleotide. The nucleic acid can be custom synthesized to contain properties that are tailored to fit a desired use. Common modifications include, but are not limited to use of locked nucleic acids (LNAs), unlocked nucleic acids (UNAs), morpholinos, peptide nucleic acids (PNA), phosphorothioate linkages, phosphonoacetate linkages, propyne analogs, 2'-O-methyl RNA, 5-Me-dC, 2'-5' linked phosphodiester linage, Chimeric Linkages (Mixed phosphorothioate and phosphodiester linkages and modifications), conjugation with lipid and peptides, and combinations thereof.

In some embodiments, the nucleic acid includes internucleotide linkage modifications such as phosphate analogs having achiral and uncharged intersubunit linkages (e.g., Sterchak, E. P. et al., *Organic Chem.*, 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Phosphorothioates (or S-oligos) are a variant of normal DNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1,2-bensodithiol-3-one 1,1-dioxide (BDTD). The latter methods avoid the problem of elemental sulfur's insolubility in most organic solvents and the toxicity of carbon disulfide. The TETD and BDTD methods also yield higher purity phosphorothioates.

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), and the like. Methods for the chemical assembly of PNAs are well known.

In some embodiments, the nucleic acid includes one or more chemically-modified heterocyclic bases including, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives, 4-acetylcytosine, 8-hydroxy-N-6-methyladenosine, aziridinylcytosine, 5-(carboxyhydroxylmethyl) uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs Inhibitory RNAs modified with 2'-flouro (2'-F) pyrimidines appear to have favorable properties in vitro.

In some embodiments the nucleic acid includes one or more sugar moiety modifications, including, but are not limited to, 2'-O-aminoethoxy, 2'-O-amonioethyl (2'-OAE), 2'-O-methoxy, 2'-O-methyl, 2-guanidoethyl (2'-OGE), 2'-O, 4'-C-methylene (LNA), 2'-O-(methoxyethyl) (2'-OME) and 2'-O—(N-(methyl)acetamido) (2'-OMA).

Methods of gene therapy typically rely on the introduction into the cell of a nucleic acid molecule that alters the genotype of the cell. Introduction of the nucleic acid molecule can correct, replace, or otherwise alters the endogenous gene via genetic recombination. Methods can include introduction of an entire replacement copy of a defective gene, a heterologous gene, or a small nucleic acid molecule such as an oligonucleotide. This approach typically requires delivery systems to introduce the replacement gene into the cell, such as genetically engineered viral vectors.

Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences necessary elements for the translation and/or transcription of the inserted coding sequence. For example, the coding sequence is preferably operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

Viral vectors include adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oligonucleotides can interact with either double-stranded or single-stranded nucleic acids. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a Kd less than 10-6, 10-8, 10-10, or 10-12. Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406.

B. Devices

In some embodiments, the purified polysaccharides can be used to prepare or form medical devices, particular devices for tissue repair, strengthening, and/or reinforcement. The materials can also be used to mimic extracellular matrices.

EXAMPLES

Example 1

Purification of Polysaccharide and Removal of Bacterial Lipopolysaccharide

The procedure was performed under a laminar flow hood that was previously cleaned with an antibacterial/antiviral solution followed by a 1 hour UV light exposure. The operator wore gloves and protective gear required for chemical and biological work to avoid product contamination and to ensure personal safety. All the solutions used were pharmaceutical grade and all tools, which were in direct contact with the product or the reagents were sterile and specified endotoxin free. A flow chart of the isolation and purification process is shown in FIG. 1.

The procedure for isolating and purifying agarose was conducted as follows:

Step 1: In order to disrupt the bacteria wall and solubilize the lipid part of the endotoxin, the agarose was incubated under agitation for two minutes in ethanol. Agarose powder was recovered by centrifugation and removal of the supernatant.

Step 2: A 0.25M solution of sodium hydroxide was used to hydrolyze the lipid-inner core bond and solubilize the polysaccharide. The free lipids were removed with an ethanol wash. The agarose was recovered by centrifugation and removal of the supernatant.

Step 3: A 0.5M solution of hydrochloride acid was used to hydrolyze the lipid/inner core bond that was not cleaved under basic conditions and to solubilize the polysaccharide. Optionally, an ethanol wash may be performed to remove free lipids. The agarose was recovered by centrifugation and removal of the supernatant.

Step 4: A second wash with a 0.25M solution of sodium hydroxide was performed for further cleavage of the lipid/inner core bound and to neutralize the acid from the previous step. The agarose was recovered by centrifugation and removal of the supernatant.

Step 5: A solution of sterile water was used for final removal of the polysaccharide and neutralization of residual acid and/or base. The agarose was recovered by centrifugation and the supernatant was removed.

Step 6: An autoclavable physiological buffer solution (Ringer Buffer) was used for final solubilization of agarose and neutralization of the acidic and basic solutions. The agarose was recovered by centrifugation and removal of the supernatant.

Step 7: The pH of the agarose suspension was adjusted to 7 and filtrated through a 40 μm pore size filter that retained the agarose but removed soluble submicron impurities.

Step 8: The volume was adjusted to 2% w/v agarose hydrogel and loaded into autoclavable syringes, which were packed in autoclave pouches prior to steam sterilization. This last step is used to sterilize the syringes and to solubilize the agarose in the syringe. After cooling, the agarose gelled, which is a convenient phase for storage. The resulting agarose loaded syringes were analyzed to assess the efficiency of the procedure.

The characterization of the agarose after the sterilization protocol involved four steps: (a) endotoxin removal was quantified; (b) the presence of microbiological organisms was assessed, (c) the amount of remaining solvent was measured and (d) the hydrogel mechanical properties were characterized.

Figure 2:
FIG. 2 is a graph showing the concentration of endotoxin (EU/ml) in commercial agarose after autoclaving (i.e., before endotoxin removal) and agarose after the purification process described herein (e.g., after endotoxin removal).

Measurement of endotoxins levels was used to assess the effectiveness of the procedure. The acceptable endotoxin level unit concentration (EU/ml) established by the Food and Drug Administration (FDA) in the United States for medical devices is 0.05 EU/ml. The endotoxin level of commercially available agarose after steam sterilization has an EU level above FDA standards. Whereas, after the endotoxin removal procedure described above and autoclaving, the endotoxins level was about 0.02 EU/ml (n=5, see FIG. 2).

Figure 3:
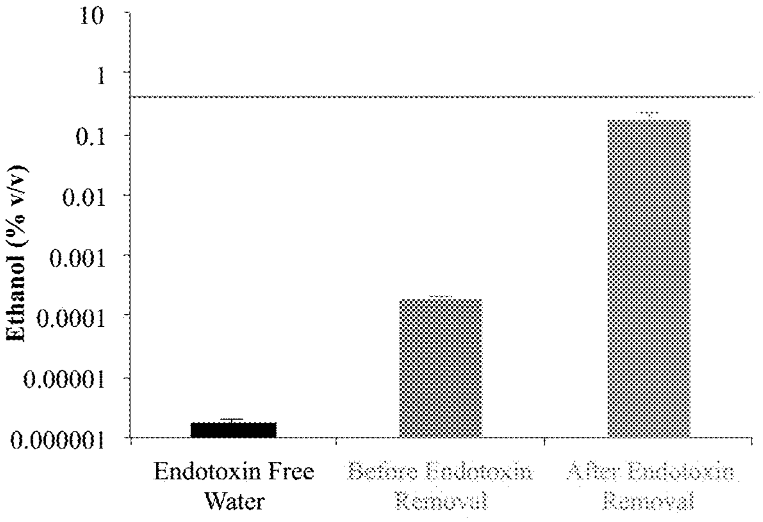
FIG. 3 is a graph showing the concentration of residual ethanol (% v/v) in commercial agarose after autoclaving (i.e., before endotoxin removal) and agarose after the purification procedure described herein (e.g., after endotoxin removal) compared to endotoxin free water.

Solvents, such as ethanol, can cause tissue damage via dehydration of cells and contact with nerves (e.g., neurolysis). Ethanol is classified as a class 3 solvent with low potential toxicity by the FDA. The maximum allowed concentration is 0.5% v/v. Since ethanol is used to sterilize agarose powder, the amount remaining in the hydrogel has to be assessed. Gas Chromatography (GC) measurement showed a concentration of 0.16% v/v (see FIG. 3).

As discussed above, the elimination of bacterial organisms can be performed using techniques known in the art, including chemical or thermal treatment as well as sterile filtration or irradiation. In order to assess if the protocol describe herein was as efficient as the industry standards, the presence of microbial contamination was monitored. After the sequential washes and autoclaving, incubation of agarose for up to a week with Luria Broth (LB) media did not show any bacterial colonies.

Optionally, sterilization using steam or gamma irradiation may be applied to the purified polysaccharide or polysaccharide derivative (i.e., agarose or agarose derivative thereof) such that the sterilization process when applied does not substantially alter the properties (i.e., gelation temperature or shear modulus) by more than 10% as compared to the properties of the polysaccharide or polysaccharide derivative prior to purification. Sterilization techniques, such as steam or gamma irradiation are well-known in the art.

The mechanical properties of the hydrogel after the procedure described herein were assessed. The entire process, purification and packaging, was performed manually, and therefore this assessment also took into account the operator error leading to variations in syringe loading. In certain embodiments, the gelation temperature and/or mechanical properties (i.e., shear modulus) of the purified polysaccharide or polysaccharide derivative (e.g., agarose or agarose derivative thereof) are the same or are substantially the same as the gelation temperature and/or mechanical properties of the polysaccharide or polysaccharide derivative prior to purification. As used herein “substantially the same” means about 10% or less relative change to the gelation temperature and/or mechanical property values of the polysaccharide or polysaccharide derivative prior to purification. Methods for determining the physical properties of polysaccharide hydrogels are known in the art. Exemplary methods are provided in Forget, et al. Proceedings of the National Academy of Sciences, 2013; 110(32):12877-12892, the disclosure of which is incorporated herein by reference.

Figure 4:
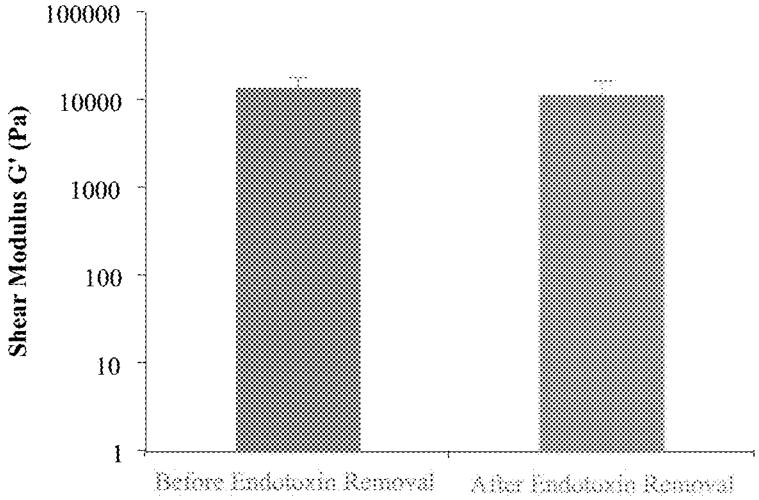
FIG. 4 is a graph showing the shear modulus G' (Pa) for commercial agarose after autoclaving (i.e., before endotoxin removal) and agarose after the purification procedure described herein.

The mechanical testing reveals that there were no significant changes in the hydrogel properties between the untreated and the purified product (n=3, see FIG. 4). This suggests that the use of acidic and basic solutions and steam sterilization does not alter the agarose backbone.

Figure 5:
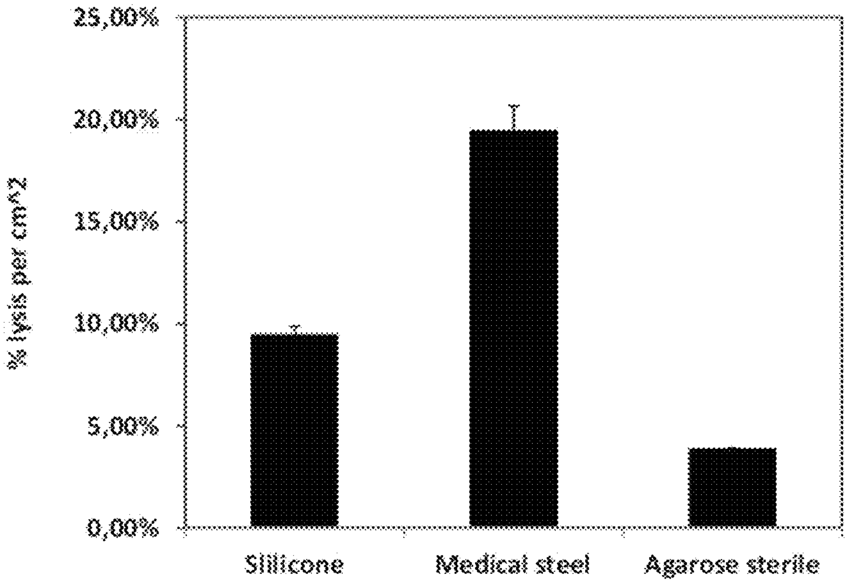
FIG. 5 is a graph showing percent lysis per $cm^2$ as a function of material.

The hemolytic properties of the agarose were compared to silicone and medical (surgical steel) using the 24 h lysis test available from HaemoScan. The results are shown in FIG. 5. The amount of lysis induced by agarose was 3.9%/$cm^2$, which is considered acceptable according to ISO 10993-4 (<5%).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A purified agarose or derivative thereof, wherein the agarose or derivative thereof contains less than 0.05 Endotoxin Units per milliliter, and wherein the agarose derivative contains one or more functional groups selected from the group consisting of carboxylate, phosphate, sulfate, sulfonate, and combinations thereof.

2. The purified agarose or derivative thereof of claim 1, wherein the agarose or derivative thereof is hydrogel-forming.

3. The purified agarose or derivative thereof of claim 2, wherein the hydrogel forms in vivo following administration to a site in a patient.

4. The purified agarose or derivative thereof of claim 1, wherein the purified agarose or derivative thereof forms a hydrogel upon contact with physiological fluids.

5. The purified agarose or derivative thereof of claim 1, wherein the agarose derivative is modified to include a peptide sequence containing arginine-glycine-aspartic acid.

6. The purified agarose or derivative thereof of claim 1, wherein the endotoxin content of the agarose or derivative thereof is determined by placing endotoxin free water on top of an equivalent volume of a 2% sample of the agarose or derivative thereof, and wherein following two days the water contains less than 0.05 Endotoxin Units per milliliter.

* * * * *